(12) United States Patent
Nishigaki

(10) Patent No.: US 9,642,595 B2
(45) Date of Patent: May 9, 2017

(54) ULTRASOUND DIAGNOSTIC APPARATUS FOR INTIMA-MEDIA THICKNESS MEASUREMENT

(75) Inventor: Morio Nishigaki, Kanagawa (JP)

(73) Assignee: KONICA MINOLTA, INC., Tokyo (JP)

(*) Notice: Subject to any disclaimer, the term of this patent is extended or adjusted under 35 U.S.C. 154(b) by 97 days.

(21) Appl. No.: 13/808,819

(22) PCT Filed: Jan. 12, 2012

(86) PCT No.: PCT/JP2012/000134
§ 371 (c)(1),
(2), (4) Date: Jan. 7, 2013

(87) PCT Pub. No.: WO2012/105162
PCT Pub. Date: Aug. 9, 2012

(65) Prior Publication Data
US 2013/0116567 A1 May 9, 2013

(30) Foreign Application Priority Data
Jan. 31, 2011 (JP) ................................ 2011-018354

(51) Int. Cl.
*A61B 8/00* (2006.01)
*A61B 8/08* (2006.01)
(Continued)

(52) U.S. Cl.
CPC .......... *A61B 8/0891* (2013.01); *A61B 8/0858* (2013.01); *A61B 8/145* (2013.01);
(Continued)

(58) Field of Classification Search
None
See application file for complete search history.

(56) References Cited

U.S. PATENT DOCUMENTS 6,132,373 A * 10/2000 Ito et al. ................. 600/437
2002/0045828 A1* 4/2002 Skidmore ................ 600/454
(Continued)

FOREIGN PATENT DOCUMENTS

CN 101677810 A 3/2010
JP 2006-00456 * 5/2006
(Continued)

OTHER PUBLICATIONS

Office Action Oct. 10, 2014 for corresponding Chinese Patent Application CN 201280002285.1 and English translation thereof.
(Continued)

*Primary Examiner* — Jonathan Cwern
*Assistant Examiner* — Amelie R Gillman
(74) *Attorney, Agent, or Firm* — Lucas & Mercanti, LLP

(57) ABSTRACT

An ultrasound diagnostic apparatus includes: a probe that transmits and receives ultrasound; a signal analysis unit that, when the probe scans a cross section of elevation direction of a blood vessel using ultrasound, detects a center scan line echo signal having passed through a center of the blood vessel among a plurality of scan line echo signals in the cross section of elevation direction of the blood vessel received by the probe, based on a part of each of the plurality of scan line echo signals that has a relatively small amplitude that corresponds to a reflected wave from a part of the blood vessel where blood flows; and an IMT measurement unit that computes an IMT from the center scan line echo signal. With this configuration, it is possible to provide an ultrasound diagnostic apparatus capable of performing wide-range IMT measurements with few errors even when a blood vessel seen from a body surface is not linear.

4 Claims, 25 Drawing Sheets

(51) Int. Cl.
*A61B 8/14* (2006.01)
*G01S 7/52* (2006.01)
*G01S 15/89* (2006.01)

(52) U.S. Cl.
CPC .......... *A61B 8/4209* (2013.01); *A61B 8/4254* (2013.01); *A61B 8/4444* (2013.01); *A61B 8/4488* (2013.01); *A61B 8/5207* (2013.01); *A61B 8/5223* (2013.01); *A61B 8/5246* (2013.01); *A61B 8/54* (2013.01); *G01S 7/52036* (2013.01); *G01S 7/52065* (2013.01); *G01S 7/52079* (2013.01); *G01S 15/8915* (2013.01); *A61B 8/42* (2013.01); *A61B 8/4245* (2013.01); *A61B 8/4281* (2013.01); *A61B 8/4466* (2013.01); *A61B 8/463* (2013.01)

(56) References Cited

U.S. PATENT DOCUMENTS

| | | | |
|---|---|---|---|
| 2003/0167005 A1* | 9/2003 | Sakuma et al. | 600/443 |
| 2005/0096528 A1* | 5/2005 | Fritz | A61B 5/02007 600/407 |
| 2007/0032725 A1 | 2/2007 | Watanabe et al. | |
| 2008/0125651 A1 | 5/2008 | Watanabe et al. | |
| 2008/0168839 A1* | 7/2008 | Katsuyama | G01S 7/52036 73/602 |
| 2008/0171939 A1* | 7/2008 | Ishihara | 600/449 |
| 2009/0163811 A1 | 6/2009 | Fukumoto et al. | |
| 2009/0204007 A1* | 8/2009 | Katoh | A61B 5/02007 600/463 |
| 2009/0253987 A1* | 10/2009 | Kim et al. | 600/438 |
| 2010/0113930 A1* | 5/2010 | Miyachi | 600/443 |
| 2010/0217125 A1 | 8/2010 | Kadokura et al. | |
| 2011/0054318 A1* | 3/2011 | Shin et al. | 600/443 |
| 2011/0077526 A1* | 3/2011 | Zwirn | A61B 5/0095 600/459 |

FOREIGN PATENT DOCUMENTS

| | | |
|---|---|---|
| JP | 2008-194364 | 8/2008 |
| WO | WO 2005/002446 | 1/2005 |
| WO | WO 2005/020821 | 3/2005 |
| WO | 2007/108359 | 3/2007 |
| WO | WO 2007/108359 | 9/2007 |
| WO | 2008/149540 | 6/2008 |
| WO | WO 2008/149540 | 12/2008 |
| WO | 2009047966 A1 | 4/2009 |

OTHER PUBLICATIONS

Office Action dated Jul. 14, 2015 for the corresponding Japanese Patent Application No. JP2012-512128.
English translation of Office Action dated Jul. 14, 2015 for the corresponding Japanese Patent Application No. JP2012-512128.
Office Action dated Apr. 24, 2015 for the corresponding Chinese Patent Application No. CN201280002285.1.
English translation of Office Action dated Apr. 24, 2015 for the corresponding Chinese Patent Application No. CN201280002285.1.
Notice of Reasons for Rejection; Japanese Patent Application No. 2012-512128; Dispatch Date: Mar. 1, 2016; total of 2 pages. English translation of Notice of Reasons for Rejection; total of 3 pages; Grand Total of 5 pages.

* cited by examiner

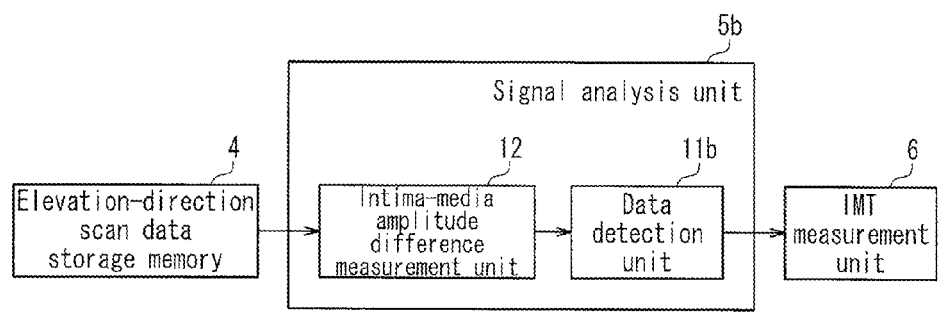
F I G. 5

A

B

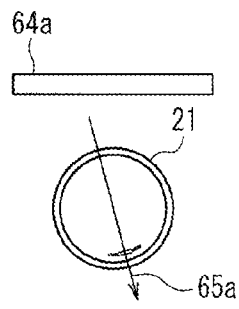
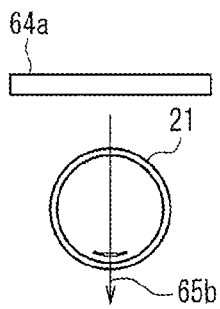
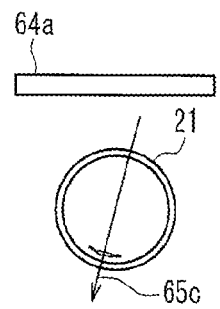
FIG. 29A              FIG. 29B              FIG. 29C
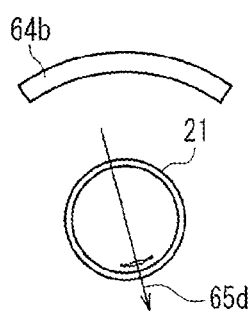
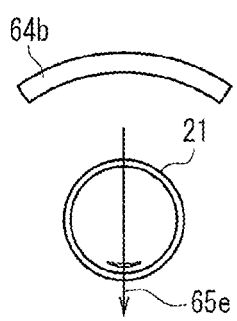
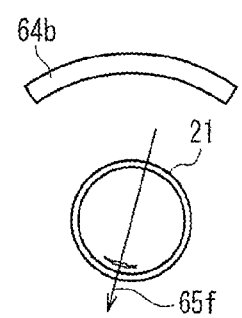
FIG. 30A              FIG. 30B              FIG. 30C

ULTRASOUND DIAGNOSTIC APPARATUS FOR INTIMA-MEDIA THICKNESS MEASUREMENT

TECHNICAL FIELD

The present invention relates to a medical ultrasound diagnostic apparatus suitable for measuring an IMT of a cervical blood vessel.

BACKGROUND ART

Ultrasound diagnostic apparatuses have been used for diagnosing many body parts related to cardiology, obstetrics and gynecology, etc., because they are noninvasive and free from radiation exposure. Recently, an IMT (Intima-Media Thickness) has received attention as an indicator of arteriosclerosis in a cervical blood vessel (carotid). As shown in FIG. 31, a cervical blood vessel 111 has a configuration in which blood 114 flows inside blood vessel walls 112, 113. Each of the blood vessel walls 112, 113 is composed of three layers of a tunica intima 115, a tunica media 116 and a tunica adventitia 117 arranged in this order from the inside. The IMT is a thickness of an intima-media complex of the blood vessel, which is obtained by converting time widths of ultrasonic echo parts of the tunica intima 115 and the tunica media 116 into distances.

FIG. 32 is a waveform diagram showing a waveform of a scan line echo signal detected from echoes of ultrasonic beams irradiated to the blood vessel. An ultrasonic probe receives echoes in the following order: a strong echo from the front wall 112, a weak echo from the blood 114, a slightly strong echo from the tunica intima 115 of the back wall 113, a weak echo from the tunica media 116 and a strong echo from the tunica adventitia 117. The IMT is proportional to time of receiving the slightly strong echo from the tunica intima 115 and the weak echo from the tunica media 116.

In the IMT measurement in conventional ultrasound diagnostic apparatuses, the array direction of a one-dimensional array probe (generally, a linear array) is matched with a longitudinal direction of the blood vessel, and an ultrasonic image such as one shown in FIG. 31 is obtained (for example, see Patent Document 1). As shown in FIG. 33, a first conventional ultrasound diagnostic apparatus 101a is composed of a probe 102, a transmission/reception unit 103, a long-axis scan data storage memory 104, a signal analysis unit 105, an IMT measurement unit 106, a scan converter 107, a display unit 108 and a control unit 109. The transmission/reception unit 103 causes the long-axis scan data storage memory 104 to store long-axis cross section data obtained by the probe 102. The signal analysis unit 105 detects data necessary for the IMT measurement among the data stored in the long-axis scan data storage memory 104. The IMT measurement unit 106 measures the IMT. The scan converter 107 combines a B-mode cross-sectional image and an IMT value, and displays the combined image on the display unit 108.

As the computation of the IMT, other than a computation using scan line echo signals themselves, there has been known a computation using an envelope shown in Patent Document 1, for example. FIG. 34 is a block diagram of a second conventional ultrasound diagnostic apparatus 101b that measures the IMT by envelope demodulation. As compared with the first conventional example, the ultrasound diagnostic apparatus 101b is provided further with a demodulator 110 that performs envelope demodulation on received scan line echo signals. FIG. 35 is a waveform diagram showing a demodulation signal obtained at the demodulator 110. The IMT measurement unit 106 computes a thickness of the intima-media part by measuring time corresponding to the slightly strong echo from the tunica intima 115 and time corresponding to the weak echo from the tunica media 116.

PRIOR ART DOCUMENT

Patent Document

Patent Document 1: JP 2008-194364 A

DISCLOSURE OF INVENTION

Problem to be Solved by the Invention

However, in the conventional ultrasound diagnostic apparatus for cervical blood vessels, since the array of the probe transducers is linear, part of the blood vessel whose intima-media can be visualized is limited when a shape of the cervical blood vessel seen from a body surface is not linear.

Further, in the conventional ultrasound diagnostic apparatus for cervical blood vessels, when a running direction of the blood vessel is not parallel to the body surface, the capability of visualizing the intima-media is reduced.

Further, in the conventional ultrasound diagnostic apparatus for cervical blood vessels, it is possible to measure the IMT only in one long-axis cross section of the blood vessel.

Thus, the conventional ultrasound diagnostic apparatus for cervical blood vessels has the above-described problems.

The present invention has been achieved to solve the conventional problems, and the object is to provide an ultrasound diagnostic apparatus capable of performing wide-range IMT measurements with few errors even when a blood vessel seen from a body surface is not linear.

Means for Solving Problem

To achieve the above object, an ultrasound diagnostic apparatus of the present invention includes: a probe that transmits and receives ultrasound; a signal analysis unit that, when the probe scans a cross section of elevation direction of a blood vessel using the ultrasound, detects a center scan line echo signal having passed through a center of the blood vessel among a plurality of scan line echo signals in the cross section of elevation direction of the blood vessel received by the probe, based on a part of each of the plurality of scan line echo signals that has a relatively small amplitude that corresponds to a reflected wave from a part of the blood vessel where blood flows; and an IMT measurement unit that computes an IMT from the center scan line echo signal.

Further, the signal analysis unit may judge, as the center scan line echo signal, a scan line echo signal whose part having a relatively small amplitude that corresponds to a reflected wave from the part of the blood vessel where blood flows is longest among a plurality of scan line echo signals in the cross section of elevation direction of the blood vessel.

Further, the signal analysis unit may judge, as the center scan line echo signal, a scan line echo signal that has a largest amplitude difference between an amplitude of a tunica intima part and an amplitude of a tunica media part among a plurality of scan line echo signals in the cross section of elevation direction of the blood vessel, the tunica intima part being positioned after the part having a relatively small amplitude that corresponds to a reflected wave from the part of the blood vessel where blood flows, and the tunica media part being positioned after the tunica intima part.

Further, the signal analysis unit may judge, as the center scan line echo signal, a scan line echo signal that has a largest ratio of an amplitude of a tunica intima part to an amplitude of a tunica media part among a plurality of scan line echo signals in the cross section of elevation direction of the blood vessel, the tunica intima part being positioned after the part having a relatively small amplitude that corresponds to a reflected wave from the part of the blood vessel where blood flows, and the tunica media part being positioned after the tunica intima part.

Further, the ultrasound diagnostic apparatus may be configured so that the signal analysis unit performs envelope demodulation on a plurality of scan line echo signals in the cross section of elevation direction of the blood vessel, computes a differential coefficient of an amplitude at a beginning of a tunica intima part, and judges, as the center scan line echo signal, a scan line echo signal that has a largest computed differential coefficient among the scan line echo signals having been subjected to the envelope demodulation, the tunica intima part being positioned after the part having a relatively small amplitude that corresponds to a reflected wave from the part of the blood vessel where blood flows.

Further, the ultrasound diagnostic apparatus may be configured so that, when the probe scans a plurality of cross sections of elevation direction of the blood vessel using the ultrasound, the signal analysis unit detects a center scan line echo signal having passed through the center of the blood vessel among scan line echo signals in each of the plurality of cross sections of elevation direction of the blood vessel received by the probe, based on the part having a relatively small amplitude that corresponds to a reflected wave from the part of the blood vessel where blood flows, and the IMT measurement unit computes an IMT from a plurality of the center scan line echo signals detected from the scan line echo signals in the plurality of cross sections of elevation direction of the blood vessel.

Further, the ultrasound diagnostic apparatus may further include a demodulator connected to the signal analysis unit, generating image data of regions shown by the respective center scan line echo signals using the center scan line echo signals, and generating, as one image, combined image data in which the respective image data are arranged side by side.

Effect of the Invention

According to the present invention, by detecting a center scan line echo signal having passed through a center of a blood vessel, it is possible to provide an ultrasound diagnostic apparatus capable of performing wide-range IMT measurements with few errors even when a blood vessel seen from a body surface is not linear.

BRIEF DESCRIPTION OF DRAWINGS

FIG. 5 is a block diagram showing a configuration of a signal analysis unit of an ultrasound diagnostic apparatus according to Embodiment 3.

FIG. 29 is a view showing a positional relationship between an array transducer, a blood vessel and an ultrasonic beam in Embodiment 11.

FIG. 30 is a view showing another positional relationship between an array transducer, a blood vessel and an ultrasonic beam in Embodiment 11.

DESCRIPTION OF THE INVENTION

Hereinafter, an ultrasound diagnostic apparatus according to embodiments of the present invention will be described with reference to the drawings.

Embodiment 1

Figure 1:
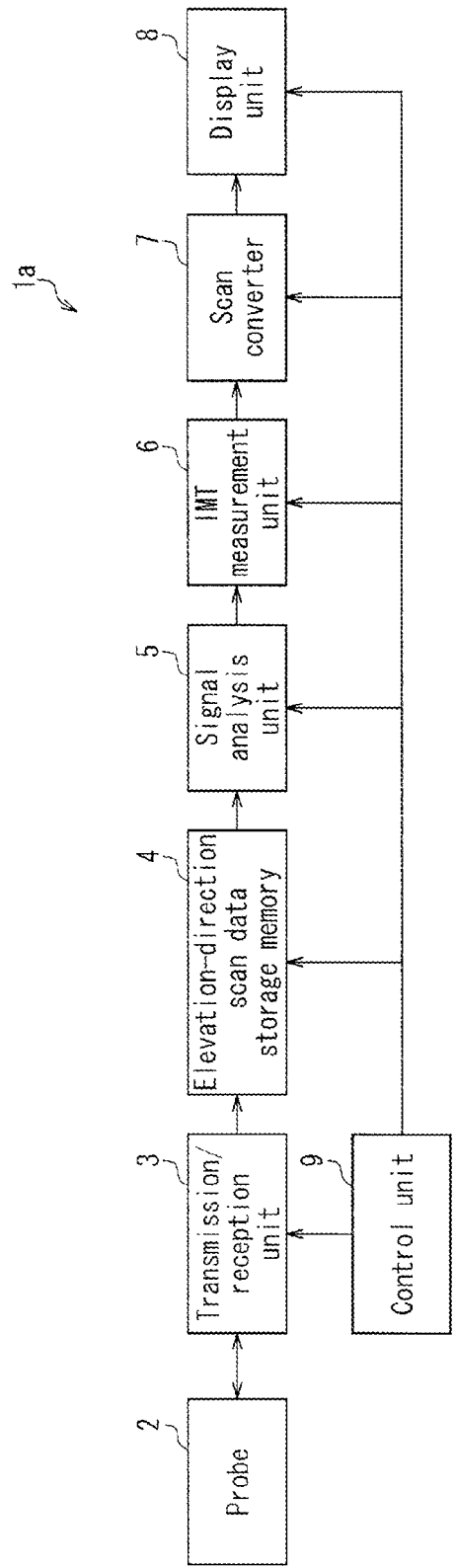
FIG. 1 is a block diagram showing a configuration of an ultrasound diagnostic apparatus according to Embodiment 1.

FIG. 1 is a block diagram showing a configuration of an ultrasound diagnostic apparatus 1a according to Embodiment 1 of the present invention. A probe 2 has a plurality of transducers (array transducer) arrayed one-dimensionally, and transmits and receives ultrasound. A transmission/reception unit 3 drives the probe 2, and controls the transmission and reception of ultrasound with respect to the probe 2. A elevation-direction scan data storage memory 4 stores scan line echo signals of ultrasonic pulses received by the probe 2. A signal analysis unit 5 selects, per scanning surface, a scan line echo signal to be subjected to an intima-media thickness measurement among the scan line echo signals stored in the elevation-direction scan data storage memory 4. Specifically, the signal analysis unit 5 selects a center scan line echo signal, i.e., a scan line echo signal of ultrasound having passed through a center of a blood vessel. An example of a blood vessel to be examined is a cervical blood vessel.

An IMT measurement unit 6 measures an intima-media thickness from each center scan line echo signal selected by the signal analysis unit 5, performs processing such as averaging on the measured intima-media thicknesses, and outputs it as an IMT value. A scan converter 7 scan-converts the scan line echo signals stored in the elevation-direction scan data storage memory 4 into B-mode image data, and generates data in which IMT measurement results (e.g., a line indicating a border between blood and a tunica intima, a position of a tunica media part, etc) are superimposed on a B-mode image. A display unit 8 displays the scan-converted data as an image. A control unit 9 controls the respective units of the ultrasound diagnostic apparatus 1a.

Next, the operation of the ultrasound diagnostic apparatus 1a configured as above will be described. First, an operator brings the probe 2 into contact with a neck surface of a subject body so that an array direction of the array transducer (i.e., a scanning plane) is orthogonal or substantially orthogonal to a running direction of a blood vessel. Next, based on the control by the control unit 9, the transmission/reception unit 3 transmits a driving signal to the probe 2 per one ultrasonic pulse. The probe 2 is driven by the driving signal, and irradiates the subject body with ultrasound. The ultrasound is reflected (echo) by the blood vessel of the subject body, and converted into an electric signal by the probe 2.

The elevation-direction scan data storage memory 4 stores scan line echo signals obtained per one ultrasonic pulse. The scan line echo signals stored in the elevation-direction scan data storage memory 4 are scan-converted by the scan converter 7, and are displayed on the display unit 8 as a B-mode image, for example. Next, the operator manually moves the probe 2 in parallel to the running direction of the blood vessel. Then, at the position where the probe 2 is moved, as described above, the ultrasound diagnostic apparatus 1a transmits and receives ultrasound, and displays the B-mode image on the display unit 8.

As described above, by performing the transmission and reception of ultrasound while moving the position of the probe 2, scan line echo signals in a plurality of scanning planes are stored in the elevation-direction scan data storage memory 4.

Figure 2:
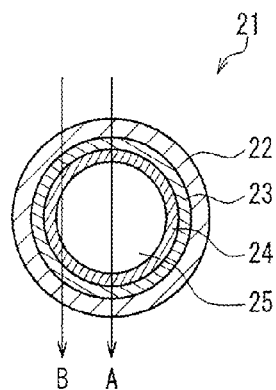
FIG. 2 is a view showing a cross-sectional configuration in an elevation direction of a blood vessel and ultrasonic beams per scan line.

FIG. 2 shows exemplary ultrasonic beams in one of the plurality of scanning planes obtained in the above-described method, illustrating a configuration of a cross section of elevation direction of a blood vessel vertical to its running direction, and ultrasonic beams per scan line. A blood vessel 21 is composed of a tunica adventitia 22, a tunica media 23 and a tunica intima 24 that are arranged in this order from the outside. Blood 25 flows inside the tunica intima 24. An ultrasonic beam A is an ultrasonic beam (center scan line) having passed through the center of the blood vessel 21, and an ultrasonic beam B is an ultrasonic beam having passed through a position displaced from the center of the blood vessel 21. Since the blood vessel 21, the tunica intima, and the tunica media are located concentrically, the ultrasonic beam A propagates vertically with respect to the respective membranes constituting the blood vessel 21. Meanwhile, the ultrasonic beam B cannot be said as propagating in the direction vertical to the respective membranes. An angle formed by the ultrasonic beam B and a tangent of each membrane at the propagation position of the ultrasonic beam B in each membrane becomes smaller with the distance from the center of the blood vessel 21.

Next, the signal analysis unit 5 detects a center scan line echo signal obtained by the ultrasonic beam A having passed through the center of the blood vessel 21 among the scan line echo signals in each scanning plane. The specific operation of detecting the center scan line echo signal obtained by the ultrasonic beam A will be described in the after-mentioned embodiments. Next, the IMT measurement unit 6 computes an intima-media thickness from the detected center scan line echo signal of the ultrasonic beam A. Consequently, intima-media thicknesses in a plurality of cross sections in a longitudinal direction of the blood vessel are obtained. Further, the IMT measurement unit 6 determines an average value or a maximum value of these intima-media thicknesses as the IMT, and the computed IMT can be displayed as a numerical value. It also is possible that the IMT measurement unit 6 computes positions of the tunica intima and the tunica media, and the scan converter 7 superimposes marks indicating the positions of the tunica intima and the tunica media on a B-mode image and displays the superimposed image on the display unit 8.

As described above, the ultrasound diagnostic apparatus according to the present embodiment can detect the center scan line echo signal obtained by the ultrasonic beam A having passed through the center of the blood vessel 21, among the scan line echo signals in each scanning plane. The intima-media thickness is detected from the detected center scan line echo signal of the ultrasonic beam A, and the IMT can be computed from the intima-media thicknesses. Thereby, even when a blood vessel seen from a body surface is not linear, wide-range IMT measurements with few errors can be performed by moving the probe 2 in the running direction of the blood vessel during scanning.

Embodiment 2

Figure 3:
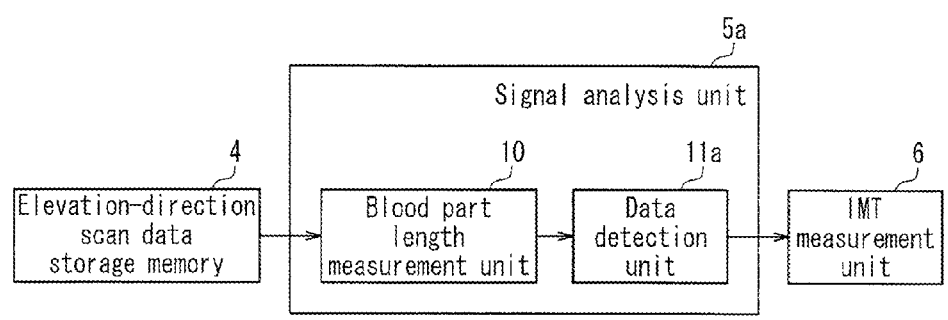
FIG. 3 is a block diagram showing a configuration of a signal analysis unit of an ultrasound diagnostic apparatus according to Embodiment 2.

An ultrasound diagnostic apparatus in Embodiment 2 of the present invention includes a signal analysis unit 5a that is configured more specifically as compared with the signal analysis unit 5 of the ultrasound diagnostic apparatus in Embodiment 1. FIG. 3 is a block diagram showing a configuration of the signal analysis unit 5a. The signal analysis unit 5a has a blood part length measurement unit 10 and a data detection unit 11a.

Figure 4A:
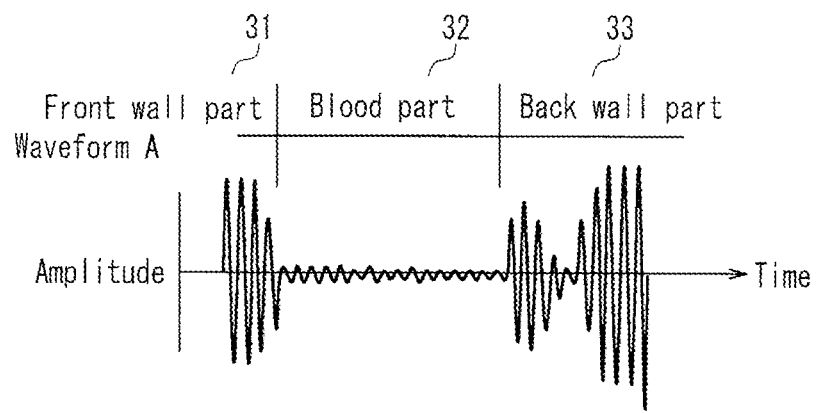
FIG. 4A is a waveform diagram showing a waveform of a scan line echo signal obtained by a reflected wave of an ultrasonic beam A in Embodiment 2.
Figure 4B:
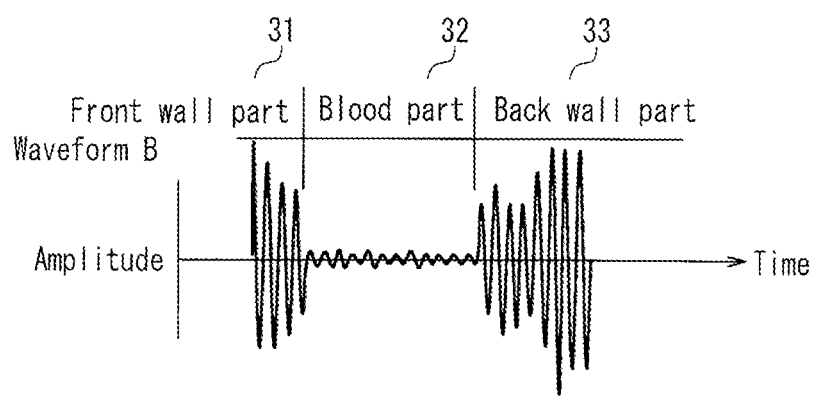
FIG. 4B is a waveform diagram showing a waveform of a scan line echo signal obtained by a reflected wave of an ultrasonic beam B in Embodiment 2.

FIG. 4A is a waveform diagram showing a waveform A of the scan line echo signal of the ultrasonic beam A having passed through the center of the blood vessel 21 shown in FIG. 2. FIG. 4B is a waveform diagram showing a waveform B of the scan line echo signal of the ultrasonic beam B shown in FIG. 2. Each of the waveform A and the waveform B has a front wall part 31 having a large amplitude corresponding to an echo reflected by a front wall (although the front wall includes the tunica intima, tunica media and tunica adventitia, they are regarded as an integral body for the sake of explanation), a blood part 32 having a small amplitude corresponding to an echo reflected by blood, and a back wall part 33 having a large amplitude corresponding to an echo reflected by a back wall. Although it depends on the individuals, amplitudes of the echoes from the front wall and the back wall are different from an amplitude of the echo from the blood, by about 20 dB. Therefore, it is possible to distinguish easily the blood part from the front wall part and the back wall part.

Since the blood vessel 21 is round in cross section as shown in FIG. 2, the waveform A shown in FIG. 4A has the blood part 32 longer than blood parts of waveforms B of ultrasonic beams B that has not passed through the center of the blood vessel 21. In other words, the scan line echo signal having the longest blood part 32 among the waveforms of the respective scan line echo signals is the scan line echo signal of the ultrasonic beam A (i.e., the center scan line echo signal). The blood part length measurement unit 10 shown in FIG. 3 measures the length of the blood part of each scan line echo signal. The data detection unit 11a detects, as the center scan line echo signal, the scan line echo signal having the longest blood part among the scan line echo signals in each scanning surface, and transmits it to the IMT measurement unit 6.

According to the configuration described above, it is possible to detect the center scan line echo signal obtained by the ultrasonic beam A having passed through the center of the blood vessel 21, among the scan line echo signals in each scanning plane. The intima-media thickness is detected from the detected center scan line echo signal of the ultrasonic beam A, and the IMT can be computed from the intima-media thicknesses. Thereby, even when a blood vessel seen from a body surface is not linear, it is possible to detect the center scan line echo signal of the ultrasonic beam having passed through the center of the blood vessel. Therefore, the intima-media thickness in each scanning surface can be detected and the IMT can be computed.

Embodiment 3

An ultrasound diagnostic apparatus in Embodiment 3 is an example in which the signal analysis unit 5 of the ultrasound diagnostic apparatus in Embodiment 1 is replaced with a signal analysis unit 5b that is different from the signal analysis unit 5a in Embodiment 2. FIG. 5 is a block diagram showing a configuration of the signal analysis unit 5b of the ultrasound diagnostic apparatus according to the present embodiment. The signal analysis unit 5b has an intima-media amplitude difference measurement unit 12 and a data detection unit 11b.

Figure 6A:
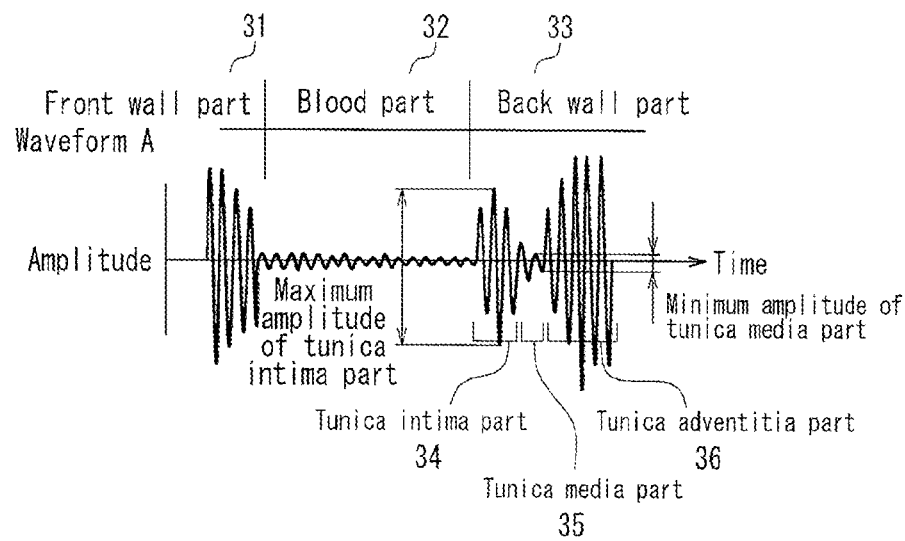
FIG. 6A is a waveform diagram showing a waveform of a scan line echo signal obtained by a reflected wave of an ultrasonic beam A in Embodiment 3.
Figure 6B:
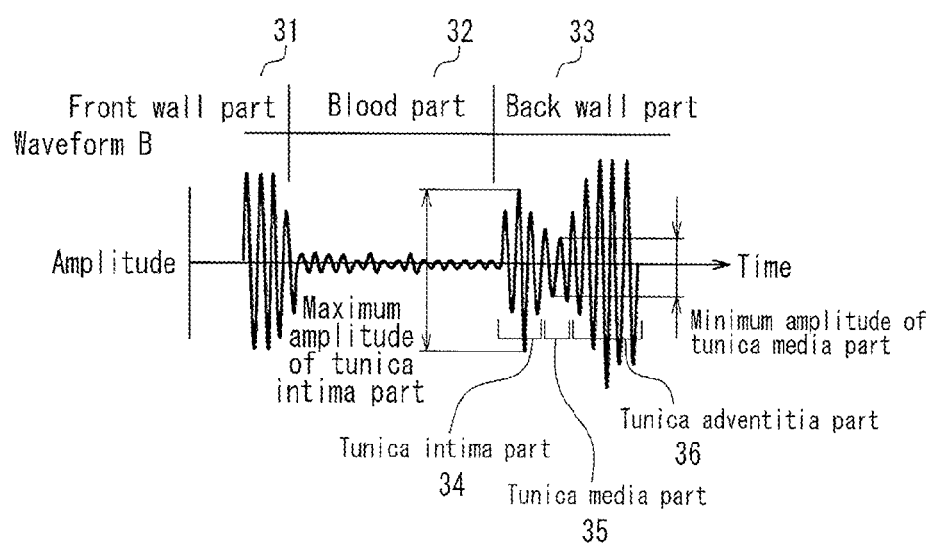
FIG. 6B is a waveform diagram showing a waveform of a scan line echo signal obtained by a reflected wave of an ultrasonic beam B in Embodiment 3.

FIG. 6A is a waveform diagram showing the waveform A of the scan line echo signal of the ultrasonic beam A having passed through the center of the blood vessel 21 shown in FIG. 2. FIG. 6B is a waveform diagram showing the waveform B of the scan line echo signal of the ultrasonic beam B shown in FIG. 2.

Each of the waveform A and the waveform B has the front wall part 31 having a large amplitude corresponding to an echo reflected by the front wall (although the front wall includes the tunica intima, tunica media and tunica adventitia, they are regarded as an integral body for the sake of explanation), the blood part 32 having a small amplitude corresponding to an echo reflected by blood, and the back wall part 33 having a large amplitude corresponding to an echo reflected by the back wall. Further, the back wall part 33 has a tunica intima part 34 corresponding to an echo reflected by the tunica intima, a tunica media part 35 corresponding to an echo reflected by the tunica media, and a tunica adventitia part 36 corresponding to an echo reflected by the tunica adventitia.

As to the ultrasonic beam A, since the ultrasonic beam is irradiated to the blood vessel wall from the vertical direction, signals from the tunica intima and tunica adventitia, which respectively are located before and after the tunica media part, are less likely to be mixed with each other. Hence, the amplitude of the tunica media part is small. Meanwhile, as to the ultrasonic beam B, since the ultrasonic beam is irradiated to the blood vessel wall from the direction displaced from the vertical direction, signals from the tunica intima and tunica adventitia, which respectively are located before and after the tunica media part, are mixed with each other. Hence, the amplitude of the tunica media part is larger than the amplitude of the tunica media part of the ultrasonic beam A. Therefore, the waveform of the ultrasonic beam A has the largest amplitude difference between a maximum amplitude of the tunica intima part 34 and a minimum amplitude of the tunica media part 35 among the waveforms of the scan line echo signals. In the ultrasonic beam A, although it depends on the individuals, the amplitude of the tunica media part is smaller than the amplitudes of the tunica intima and tunica adventitia parts by 3-6 dB or more in the case of inspecting a healthy subject body without blood vessel lesion, etc. Therefore, the tunica media part can be recognized easily. Meanwhile, in the ultrasonic beam B, as compared with this, there is less amplitude difference between the tunica media part and the tunica intima/tunica adventitia parts, or there is no amplitude difference therebetween depending on the situation. Therefore, the tunica media part sometimes cannot be recognized.

Figure 10A:
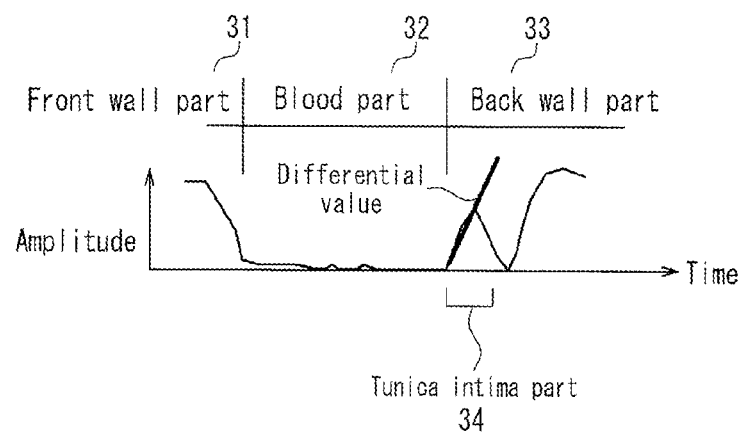
FIG. 10A is a waveform diagram showing a waveform obtained by demodulating the scan line echo signal obtained by the reflected wave of the ultrasonic beam A in Embodiment 4.

The intima-media amplitude difference measurement unit 12 computes, per scan line, an envelope of the scan line echo signal shown in FIG. 10A, and judges, as the maximum amplitude of the tunica intima part 34, an amplitude at a part of the tunica intima part 34 firstly exhibiting a maximal value after the blood part having a small amplitude. Further, the intima-media amplitude difference measurement unit 12 judges, as the minimum amplitude of the tunica media part 35, an amplitude at a part of the tunica media part 35 firstly exhibiting a minimal value after the maximum amplitude of the tunica intima part 34. Then, the intima-media amplitude difference measurement unit 12 measures a difference between the maximum amplitude of the tunica intima part 34 and the minimum amplitude of the tunica media part 35. The data detection unit 11b detects, as the center scan line echo signal, the scan line echo signal having the largest amplitude difference between the maximum amplitude of the tunica intima part 34 and the minimum amplitude of the tunica media part 35, and transmits it to the IMT measurement unit 6.

According to the configuration described above, it is possible to detect the center scan line echo signal obtained by the ultrasonic beam A having passed through the center of the blood vessel 21, among the scan line echo signals in each scanning plane. The intima-media thickness is detected from the detected center scan line echo signal of the ultrasonic beam A, and the IMT can be computed from the intima-media thicknesses. Thereby, even when a blood vessel seen from a body surface is not linear, it is possible to detect the center scan line echo signal of the ultrasonic beam having passed through the center of the blood vessel. Therefore, the intima-media thickness in each scanning surface can be detected and the IMT can be computed.

Figure 7:
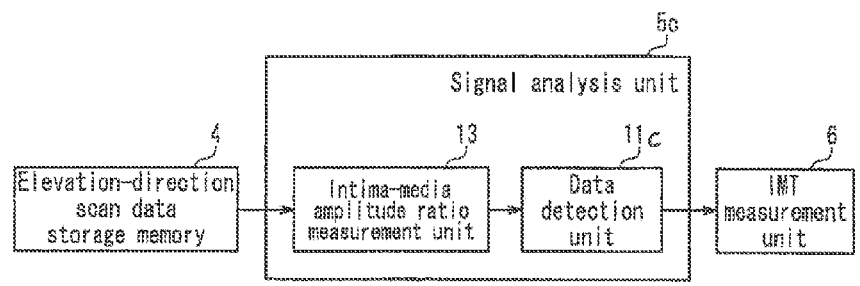
FIG. 7 is a block diagram showing another configuration of the signal analysis unit in the ultrasound diagnostic apparatus according to Embodiment 3.

FIG. 7 is a block diagram showing a signal analysis unit 5c that is another configuration of the signal analysis unit 5 in the ultrasound diagnostic apparatus according to the present embodiment. In place of the intima-media amplitude difference measurement unit 12, the signal analysis unit 5c has an intima-media amplitude ratio measurement unit 13 that measures, per scan line, a ratio of the maximum amplitude of the tunica intima part 34 to the minimum amplitude of the tunica media part 35. A data detection unit 11c detects, as the center scan line echo signal, the scan line echo signal having the largest ratio of the maximum amplitude of the tunica intima part 34 to the minimum amplitude of the tunica media part 35, and transmits it to the IMT measurement unit 6.

Also with this configuration, similarly to the above-described ultrasound diagnostic apparatus having the signal analysis unit 5b shown in FIG. 5, it is possible to detect the center scan line echo signal of the ultrasonic beam having passed through the center of the blood vessel even when a blood vessel seen from a body surface is not linear. Thereby, the intima-media thickness in each scanning surface can be detected and the IMT can be computed.

Embodiment 4

Figure 8:
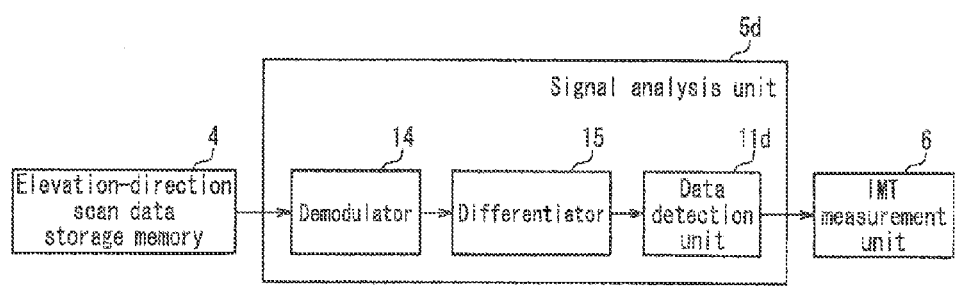
FIG. 8 is a block diagram showing a configuration of a signal analysis unit of an ultrasound diagnostic apparatus according to Embodiment 4.

An ultrasound diagnostic apparatus in Embodiment 4 includes, regarding the signal analysis unit 5 of the ultrasound diagnostic apparatus in Embodiment 1, a signal analysis unit 5d different from those in Embodiments 2 and 3. FIG. 8 is a block diagram showing a configuration of the signal analysis unit 5d of the ultrasound diagnostic apparatus according to the present embodiment. The signal analysis unit 5d has a demodulator 14, a differentiator 15, and a data detection unit 11d.

Figure 9:
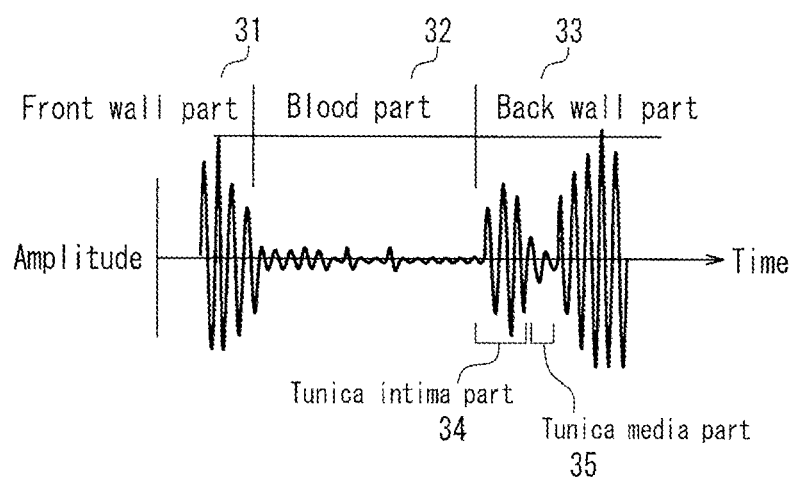
FIG. 9 is a waveform diagram showing a waveform of a scan line echo signal obtained by a reflected wave of an ultrasonic beam A in Embodiment 4.
Figure 10B:
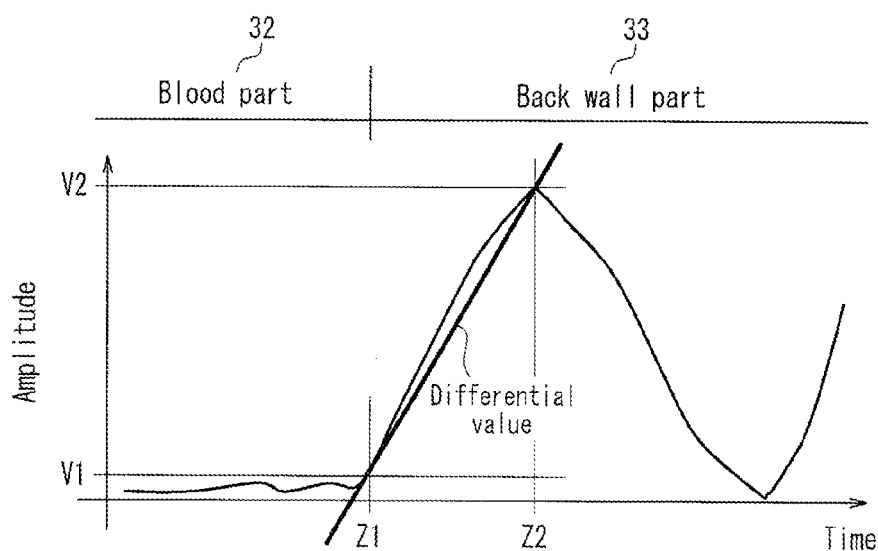
FIG. 10B is an enlarged view of a rising edge part of the scan line echo signal after a blood part in FIG. 10A.

FIG. 9 is a waveform diagram showing the waveform A of the scan line echo signal of the ultrasonic beam A having passed through the center of the blood vessel 21 shown in FIG. 2. The demodulator 14 performs envelope demodulation on the waveform A. FIG. 10A is a waveform diagram showing a waveform obtained by demodulating the waveform A. FIG. 10B is an enlarged view of the back wall part 33 in FIG. 10A.

As in the ultrasonic beam A, when ultrasonic beams are irradiated vertically to the blood vessel wall, a rising edge of the waveform caused by reflection of the intima surface is sharp. Meanwhile, as in the ultrasonic beam B, when ultrasonic beams are irradiated to the blood vessel wall from the direction displaced from the vertical direction, the rising edge of the waveform caused by reflection of the intima surface is gentle, also considering that the ultrasonic beam has a certain amount of thickness.

The differentiator 15 shown in FIG. 8 detects, in each scan line echo signal having been subjected to the envelope demodulation shown in FIG. 10B, a position (Z1) where the scan line echo signal exceeds a certain threshold (V1) after the blood part 32. The differentiator 15 further detects an amplitude (V2) and a position (Z2) where the scan line echo signal becomes maximal, and computes $(V2-V1)/(Z2-Z1)$ as a differential coefficient of the rising edge of the waveform. The data detection unit 11d detects, as the center scan line echo signal, the scan line echo signal having the largest differential coefficient of the rising edge among the scan line echo signals in one scanning surface, and transmits it to the IMT measurement unit 6.

According to the configuration described above, it is possible to detect the center scan line echo signal obtained by the ultrasonic beam A having passed through the center of the blood vessel 21, among the scan line echo signals in each scanning plane. The intima-media thickness can be detected from the detected center scan line echo signal of the ultrasonic beam A, and the IMT can be computed from the intima-media thicknesses. Thereby, even when a blood vessel seen from a body surface is not linear, it is possible to detect the center scan line echo signal of the ultrasonic beam having passed through the center of the blood vessel. Therefore, the intima-media thickness in each scanning surface can be detected and the IMT can be computed.

Embodiment 5

Figure 11:
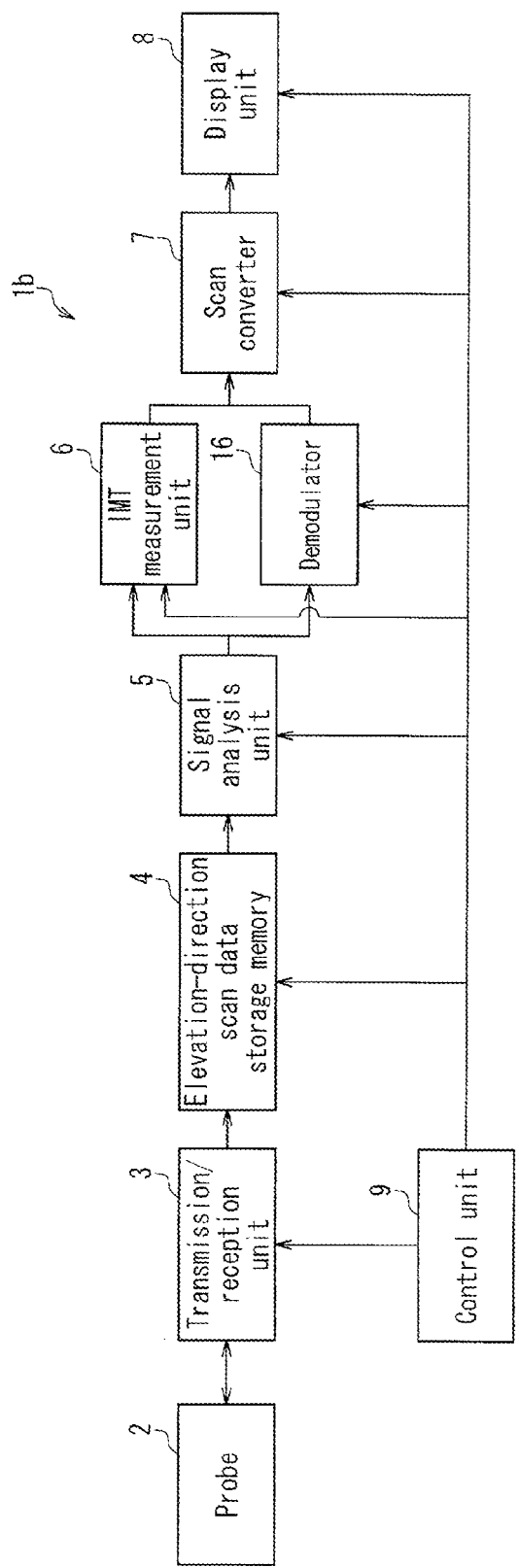
FIG. 11 is a block diagram showing a configuration of an ultrasound diagnostic apparatus according to Embodiment 5.

FIG. 11 is a block diagram showing a configuration of an ultrasound diagnostic apparatus 1b according to Embodiment 5 of the present invention. The ultrasound diagnostic apparatus 1b has a configuration in which a demodulator 16 is arranged parallel to the IMT measurement unit 6 of the ultrasound diagnostic apparatus 1 according to Embodiment 1. The demodulator 16 performs demodulation for B-mode images.

Next, the operation of the ultrasound diagnostic apparatus 1b will be described. First, the probe 2 receives echoes from the subject body by means of the transmission/reception unit 3, and the elevation-direction scan data storage memory 4 stores scan line echo signals. This operation is repeated while the operator changes the position of the probe 2 along the blood vessel. The signal analysis unit 5 detects a center scan line echo signal obtained by the ultrasonic beam having passed through the center of the blood vessel among the scan line echo signals in each scanning plane. The IMT measurement unit 6 computes an intima-media thickness per the detected center scan line echo signal, and determines an average value or a maximum value of these intima-media thicknesses as the IMT.

Figure 12:
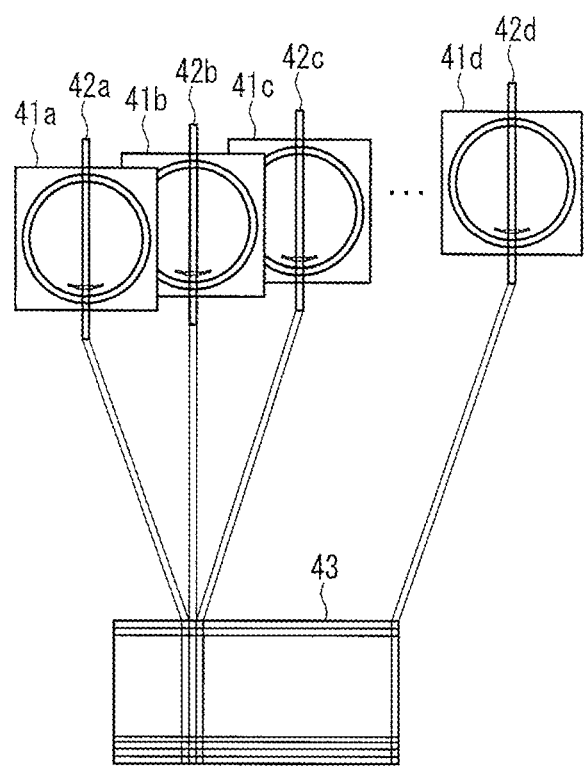
FIG. 12 shows B-mode images in respective scanning surfaces, and a combined image in which images of center regions of the respective scanning surfaces are combined.

The demodulator 16 generates partial B-mode images of the center scan line echo signals that have pass through the center of the blood vessel. The top of FIG. 12 shows B-mode images in the respective scanning surfaces. Center regions 42a-42d passing through the center of the blood vessel in B-mode images 41a-41d are images generated by the demodulator 16. The demodulator 16 generates a combined image in which images of the center regions of the respective scanning surfaces are placed side by side. The bottom of FIG. 12 shows a combined image 43 in which the images of the center regions of the respective scanning surfaces are combined. This combined image 43 looks like a conventional image obtained by scanning the long-axis cross section of the blood vessel. However, in the conventional method, when the blood vessel is tortuous, part of the blood vessel cannot be displayed. Meanwhile, in this method, the images of the center regions of all the scanning regions can be displayed.

Next, the scan converter 7 scan-converts data of the combined image 43 so that the data can be displayed on the display unit 8. The display unit 8 displays the scan-converted data as the combined image.

As described above, even when a blood vessel seen from a body surface is not linear, the ultrasound diagnostic apparatus according to the present embodiment can measure the IMT with few errors in the wide range of the blood vessel by moving the probe 2 in the running direction of the blood vessel during scanning.

Further, even when the blood vessel is tortuous, it is possible to display a combined image in which images of center regions in the respective scanning regions are combined.

Further, by displaying the combined image in which images of blood center regions are combined, it is possible to understand the measured intima-media thickness easily.

Embodiment 6

Figure 13:
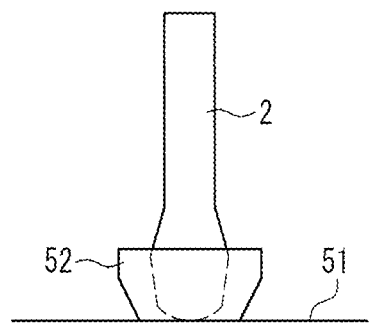
FIG. 13 is a side view showing a configuration of a probe of an ultrasound diagnostic apparatus according to Embodiment 6.

FIG. 13 is a side view showing a configuration of a probe of an ultrasound diagnostic apparatus according to Embodiment 6 of the present invention. The ultrasound diagnostic apparatus according to the present embodiment has the same configuration as the ultrasound diagnostic apparatus according to Embodiment 1, except that an attachment is provided at a tip of the probe. The explanation of the same constituent elements will be omitted.

Figure 14:
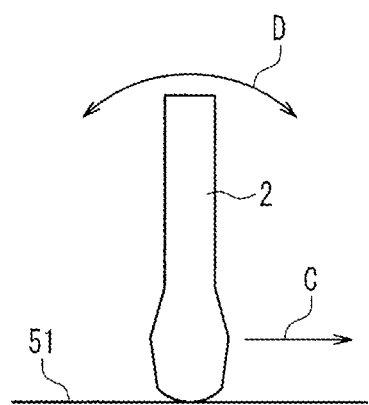
FIG. 14 is a side view showing a state of the probe during the movement.

A sled-shaped attachment 52 is attached to the tip of the probe 2. If the attachment 52 is not provided, the probe 2 tends to be displaced in a direction indicated by an arrow D as shown in FIG. 14 when moved manually in a direction of an arrow C. This makes an angle formed between the probe 2 and the surface of the subject body 51 unstable.

By using the sled-shaped attachment 52, an contact area between the subject body 51 and the probe 2 is increased, and thus the angle between the probe 2 and the surface of the subject body 51 can be kept stably.

Incidentally, the sled-shaped attachment 52 may be attached to the probes of the ultrasound diagnostic apparatuses according to Embodiments 2-5. In the present embodiment, although the attachment having a sled shape is mounted to the probe, it need not have a sled shape, and may have any shape such as a flat-plate shape and a cross shape, as long as it allows the probe to move stably.

Embodiment 7

Figure 15:
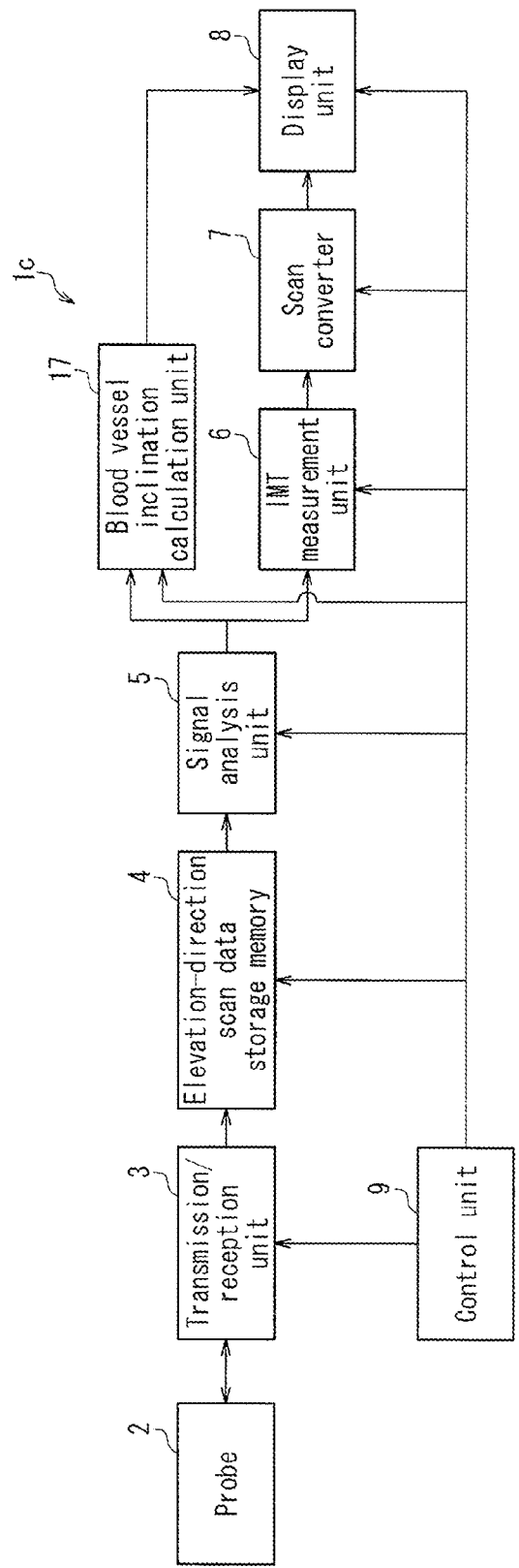
FIG. 15 is a block diagram showing a configuration of an ultrasound diagnostic apparatus according to Embodiment 7.

FIG. 15 is a block diagram showing a configuration of an ultrasound diagnostic apparatus 1c according to Embodiment 7 of the present invention. In the ultrasound diagnostic apparatus 1c according to the present embodiment, a blood vessel inclination calculation unit 17 is arranged between the signal analysis unit 5 and the display unit 8, as compared with the ultrasound diagnostic apparatus 1a according to Embodiment 1.

Figure 16:
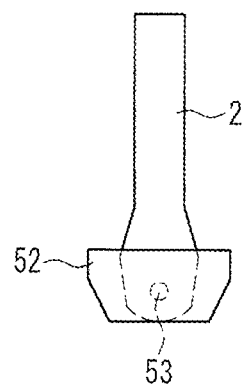
FIG. 16 is a side view showing a configuration of a probe in Embodiment 7.

FIG. 16 is a side view showing a configuration of a probe of the ultrasound diagnostic apparatus 1c according to the present embodiment. As compared with the ultrasound diagnostic apparatus 1a according to Embodiment 1, the ultrasound diagnostic apparatus 1c is provided with an attachment at the tip of the probe. The ultrasound diagnostic apparatus 1c has the same configuration as the ultrasound diagnostic apparatus 1a according to Embodiment 1, except for the above-described blood vessel inclination calculation unit 17 and the attachment. The explanation of the same constituent elements will be omitted.

The sled-shaped attachment 52 that is attached to the tip of the probe 2 includes a rotation shaft 53 that supports the probe 2 movably and a fixing portion (not shown) that stops the rotation of the probe 2 at a desired angle. By utilizing the rotation shaft 53 and the fixing portion, the probe 2 can be set to incline at a certain angle with respect to the attachment 52.

Figure 17:
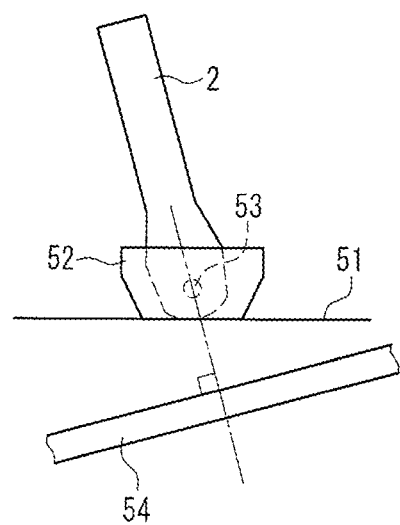
FIG. 17 shows a state of measuring the IMT of a blood vessel using the probe in Embodiment 7.

FIG. 17 shows a state of measuring the IMT of the blood vessel using the probe 2 according to the present embodiment. The running direction of the blood vessel 54 is not always parallel to the body surface 51 of the subject body. By inclining the probe 2 with respect to the attachment 52 and supporting the probe 2 thereby, the probe 2 can be inclined stably relative to the vertical direction of the body surface 51. Therefore, ultrasonic beams can be irradiated vertically to the running direction of the blood vessel 54.

The blood vessel inclination calculation unit 17 shown in FIG. 17 computes, e.g., the inclination of the running direction of the blood vessel with respect to the body surface 51 from the position of the front wall of the blood vessel in each scanning region.

Next, the operation of the ultrasound diagnostic apparatus according to the present embodiment will be described. In the present embodiment, the IMT is measured by scanning the entire scanning region twice manually. First, as the first scanning, the angle of ultrasonic beams is set to be vertical to the body surface. Next, the probe 2 receives reflected waves from the subject body by means of the transmission/reception unit 3, and the elevation-direction scan data storage memory 4 stores scan line echo signals. This operation is performed at each position where the probe 2 is moved manually by the operator along the blood vessel. Next, the signal analysis unit 5 detects the scan line echo signal obtained by the ultrasonic beam having passed through the center of the blood vessel among the scan line echo signals in each scanning plane.

Next, the IMT measurement unit 6 computes intima-media thicknesses from the detected scan line echo signals, and determines an average value or a maximum value of these intima-media thicknesses as the IMT. Further, the blood vessel inclination calculation unit 17 computes the depth of the blood vessel from the body surface in each scanning position by detecting the position of, e.g., the tunica adventitia part of the front wall part of each scan line echo signal, and computes the inclination of the running direction of the blood vessel with respect to the body surface based on the change in the depth of the blood vessel. The display unit 8 displays the computed data. When the inclination of the running direction of the blood vessel is zero, i.e., the blood vessel is irradiated with ultrasonic beams vertically, the second scanning need not be performed. The IMT measurement unit 6 causes the display unit 8 to display the IMT value, and the operation is completed.

When the blood vessel inclination calculation unit 17 judges that the blood vessel inclines with respect to the vertical direction of ultrasonic beams, it causes the display unit 8 to display the inclined angle. The operator inclines the probe 2 with respect to the attachment 52 by the angle displayed on the display unit 8. Then, the second scanning is performed. The IMT measurement unit 6 computes intima-media thicknesses from the second scan line echo signals, determines an average value or a maximum value of these intima-media thicknesses as the IMT, and causes the display unit 8 to display the IMT value via the scan converter 7. The operation is completed.

As described above, the ultrasound diagnostic apparatus according to the present embodiment can measure the IMT even when the blood vessel is not parallel to the body surface.

Embodiment 8

Figure 18:
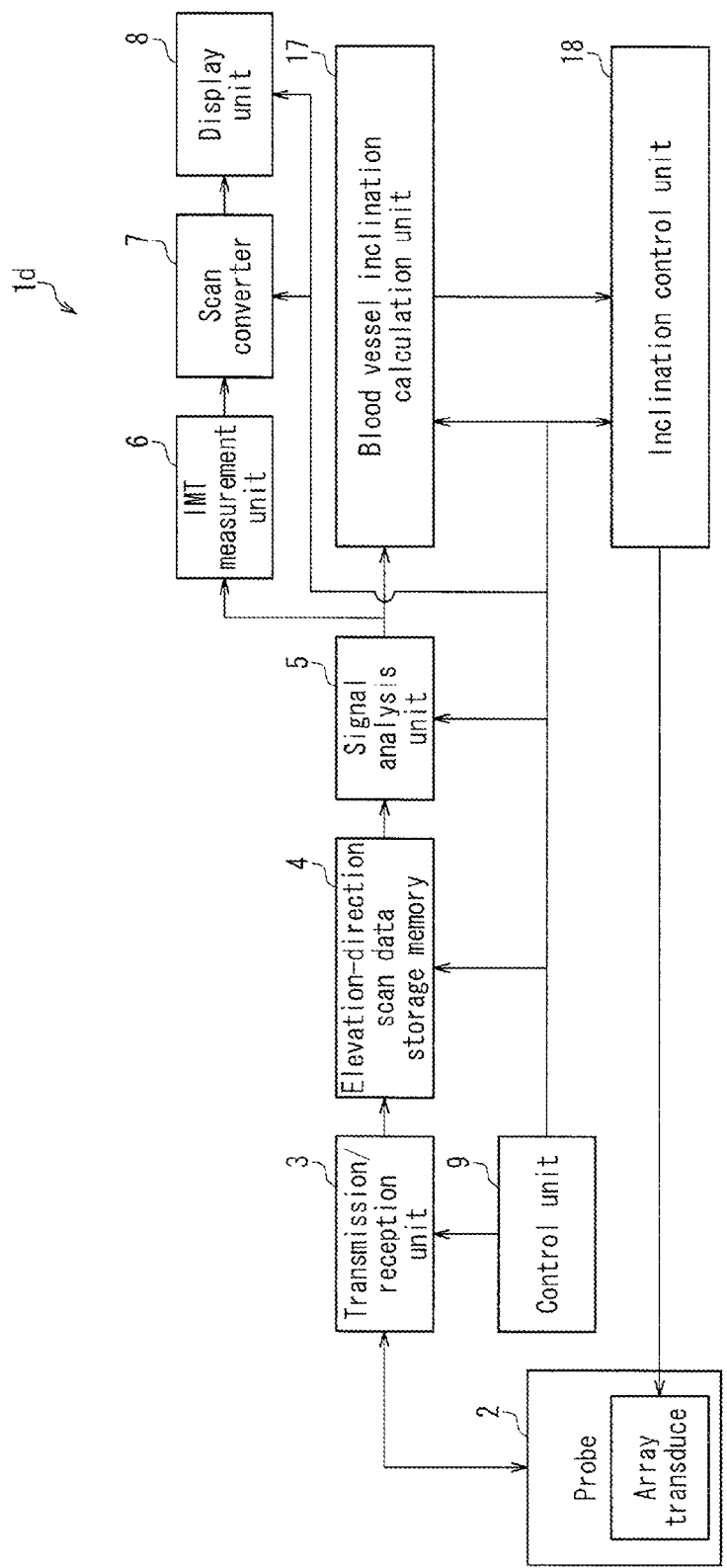
FIG. 18 is a block diagram showing a configuration of an ultrasound diagnostic apparatus according to Embodiment 8.

FIG. 18 is a block diagram showing a configuration of an ultrasound diagnostic apparatus 1*d* according to Embodiment 8 of the present invention. The ultrasound diagnostic apparatus 1*d* according to the present embodiment has an inclination control unit 18, as compared with the ultrasound diagnostic apparatus 1*c* according to Embodiment 7.

Figure 19:
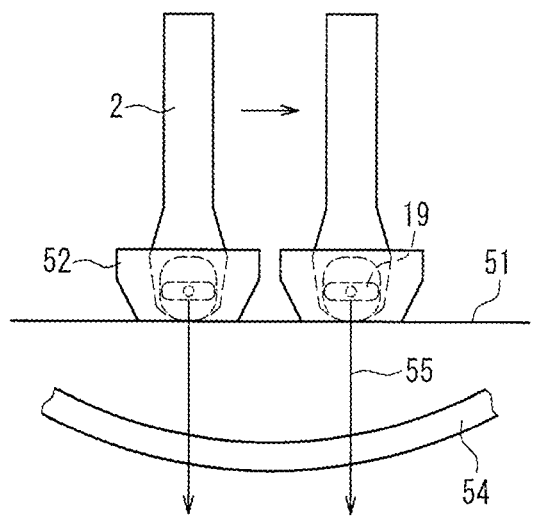
FIG. 19 is a side view showing a configuration of a probe in Embodiment 8.

FIG. 19 is a side view showing a configuration of a probe of the ultrasound diagnostic apparatus 1*d* according to the present embodiment. The ultrasound diagnostic apparatus 1*d* is different from the ultrasound diagnostic apparatus 1*c* in that the array transducer arranged in the probe 2 is replaced with a rotatable array transducer 19.

The ultrasound diagnostic apparatus 1*c* performs the second scanning by inclining the entire probe 2 in accordance with the inclination of the blood vessel, whereas the ultrasound diagnostic apparatus 1*d* performs the second scanning by inclining the array transducer 19 in accordance with the inclination of the blood vessel. The ultrasound diagnostic apparatus 1*d* has the same configuration as the ultrasound diagnostic apparatus 1*c* according to Embodiment 7, except for the above-described configuration. The explanation of the same constituent elements will be omitted.

The sled-shaped attachment 52 is fixed so that the probe 2 is not inclined from the direction vertical to the body surface. Inside the probe 2, the array transducer 19 is arranged rotatably. The inclination control unit 18 controls the inclination of the array transducer 19 in accordance with the inclination of the blood vessel. As an exemplary method for controlling the inclination of the array transducer 19, the following mechanical scanning technique, which is well-known in the field of the ultrasound diagnostic apparatus, can be used: providing a rotation shaft in the array transducer; supporting the rotation shaft by the main body of the probe 2; providing a control means such as a motor for controlling the rotation direction of the array transducer; filling a gap between the array transducer and the probe 2 with an acoustic coupling liquid for improving acoustic matching; and rotating the array transducer by the control means.

Next, the operation of the ultrasound diagnostic apparatus 1*d* according to the present embodiment will be described. First, as the first scanning, the array transducer 19 is arranged to face directly below so that the angle of ultrasonic beams 55 is vertical to the body surface. In this state, the first scanning is performed in the same manner as in Embodiment 7. The blood vessel inclination calculation unit 17 detects an inclination of the blood vessel with respect to the body surface in each scanning position, and the inclination control unit 18 stores the inclination in each position. Thereby, it is possible to detect the inclination of the blood vessel 54 with respect to the body surface 51, that is, the bent state of the blood vessel.

Figure 20:
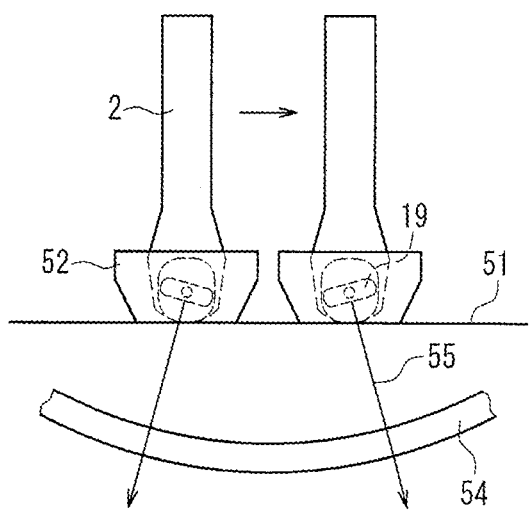
FIG. 20 is a side view showing a configuration of the probe in the second scanning in Embodiment 8.

Next, as shown in FIG. 20, the second scanning is performed. At this time, the inclination control unit 18 changes the orientation of the array transducer 19 in accordance with the inclination of the blood vessel in each scanning position so that the ultrasonic beams 55 are irradiated to the blood vessel vertically.

As described above, the ultrasound diagnostic apparatus according to the present embodiment can measure the IMT even when the blood vessel is not parallel to the body surface. Further, even when the blood vessel is bent, the IMT can be measured.

Embodiment 9

In Embodiments 7 and 8, the scanning region is scanned twice. In this case, if the moving distance of the probe 2 is not displayed clearly, the scanning position will be displaced between the first scanning and the second scanning when the probe 2 is scanned twice manually. An ultrasound diagnostic apparatus according to the present embodiment solves this problem.

Figure 21:
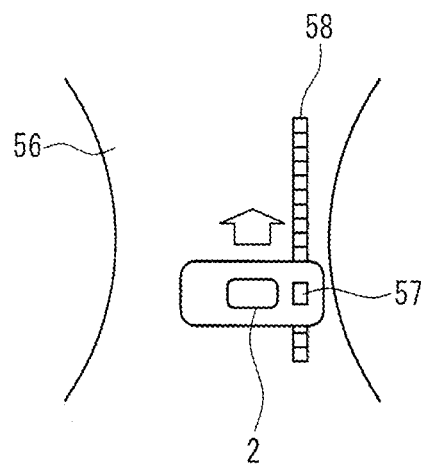
FIG. 21 is a top view showing a state in which a probe is brought into contact with a neck in Embodiment 9.

FIG. 21 is a top view showing a state in which the probe 2 is brought into contact with a neck 56. A tape 58 for specifying a position (e.g., tape with stripe pattern) is attached to the neck 56. A photoelectronic sensor 57 for irradiating a subject with light and reading the reflected light is arranged on the probe 2. The photoelectronic sensor 57 reads information of the tape 58 (e.g., information on the contrast of the reflected light when using the tape with stripe pattern) attached to the neck 56, and detects the position of the probe 2.

With the configuration described above, it is possible to eliminate the displacement between the position of the first scanning and the position of the second scanning. Thereby, ultrasonic beams can be irradiated to the blood vessel vertically, and the IMT can be measured accurately.

Embodiment 10

Figure 22:
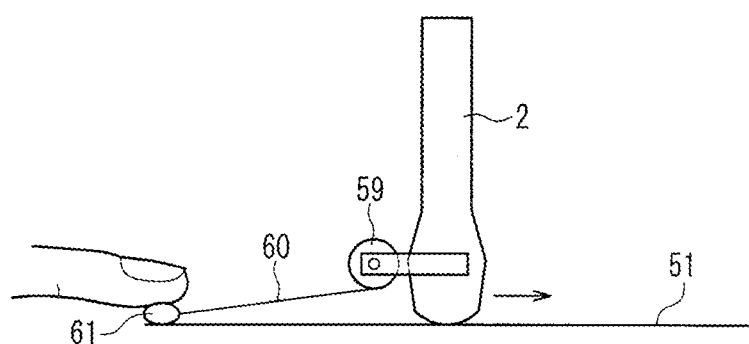
FIG. 22 is a side view showing a configuration of an ultrasound diagnostic apparatus according to Embodiment 10.

An ultrasound diagnostic apparatus according to Embodiment 10 of the present invention is another example that solves the same problem as that described in Embodiment 9. FIG. 22 is a side view showing a configuration of the ultrasound diagnostic apparatus according to the present embodiment. A bobbin 59 for taking up a wire 60 is attached to the probe 2. When the wire 60 is pulled out, the bobbin 59 rotates. An encoder (not shown) is attached to the bobbin 59. By detecting the rotation of the bobbin 59, the encoder detects the pulled-out length of the wire 60. A stopper 61 is attached at an end of the wire 60. By holding the stopper 61 using a finger of the operator for example, the stopper 61 serves as a base point for detecting the position of the probe 2.

In the IMT measurement using the ultrasonic probe according to the present embodiment, first, the stopper 61 is fixed, and the first scanning is performed while the wire 60 is pulled out from the bobbin 59. At this time, the encoder detects each scanning position of the probe by detecting the wire length. Next, the wire 60 is taken up by the bobbin 59, with the stopper 61 being fixed.

Next, the second scanning is performed while the wire is pulled out along the first scanning path. At this time, a control portion (not shown) performs the scanning at each scanning position of the first scanning.

With the configuration described above, it is possible to eliminate the displacement between the position of the first scanning and the position of the second scanning. Thereby, ultrasonic beams can be irradiated to the blood vessel vertically, and the IMT can be measured accurately.

Figure 23:
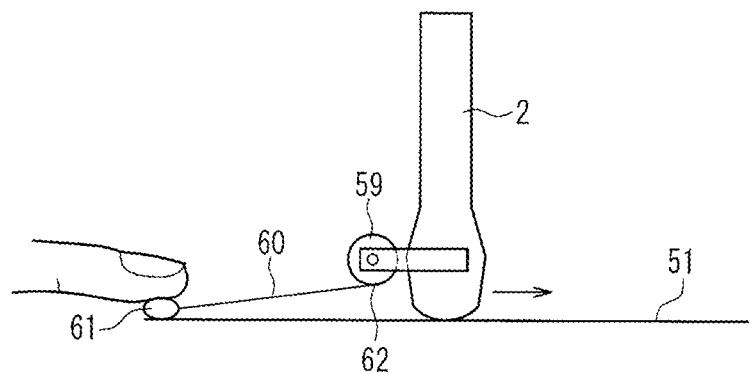
FIG. 23 is a side view showing another configuration of the ultrasound diagnostic apparatus according to Embodiment 10.

Further, as shown in FIG. 23, the ultrasonic probe further may have a contact point sensor 62 that detects a position (contact point) where the wire 60 is separated from the bobbin 59. The contact point sensor 62 can be provided anywhere, such as inside the bobbin 59 and at a support portion that supports the bobbin 59 to the probe 2. The position of the contact point is associated with the inclination of the probe 2. For example, in FIG. 23, when the probe 2 is inclined to the left, the position of the bobbin 59 slightly moves in a lower left direction, which moves the position of the contact point clockwise. In other words, the inclination of the probe 2 can be detected from the position of the contact point that is detected by the contact point sensor 62.

Based on the inclination of the probe 2 detected by the movement of the probe 2 in the first scanning and the inclination of the blood vessel with respect to the body surface 51, the inclination control unit 18 computes an inclination of the probe 2 that allows ultrasonic beams to be vertical to the running direction of the blood vessel. This inclination may be displayed on the display unit in the second scanning for allowing the operator to operate the probe 2. When the probe 2 has the attachment shown in FIG. 16, it may be inclined by the attachment in accordance with the movement of the probe 2.

As described above, according to this configuration, it is possible to detect not only the scanning position of the probe 2 but also the inclination of the probe 2 at the time of the scanning. Therefore, the vertical cross section of the blood vessel can be scanned with high accuracy, and the IMT can be measured accurately.

Figure 24:
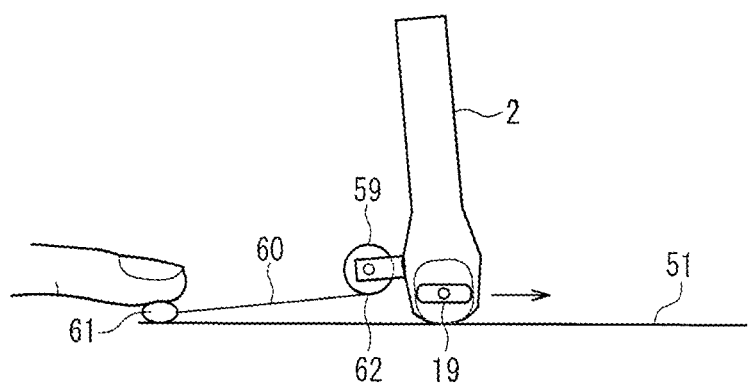
FIG. 24 is a side view showing another configuration of the ultrasound diagnostic apparatus according to Embodiment 10.

Further, as shown in FIG. 24, the array transducer may be a rotatable array transducer 19. According to this configuration, the contact point sensor 62 detects an inclination of the probe 2 in the first scanning, and the inclination control unit 18 computes the inclination of the probe 2 that allows ultrasonic beams to be vertical to the running direction of the blood vessel. The inclination control unit 18 rotates the array transducer 19 in accordance with the inclination of the probe 2 at the second scanning, thereby correcting the inclination of the probe 2. Thus, ultrasonic beams can be irradiated to the blood vessel vertically.

Figure 25:
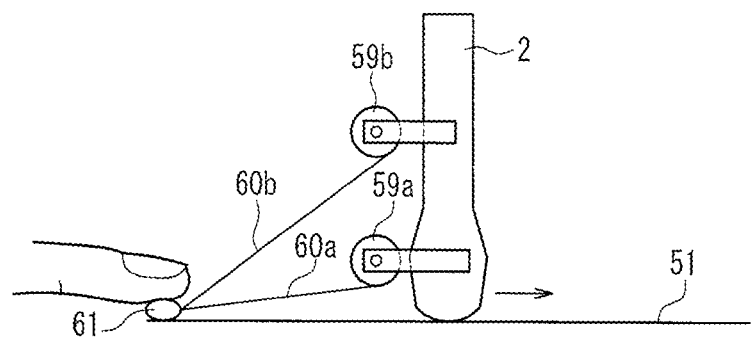
FIG. 25 is a side view showing another configuration of the ultrasound diagnostic apparatus according to Embodiment 10.

Further, as shown in FIG. 25, the ultrasonic probe may have a configuration in which the contact point sensor is not provided but two sets of combinations (wire length detection mechanisms) of bobbins 59*a*, 59*b* and encoders are provided at different positions in the height direction of the probe 2. Also in this configuration, similarly to FIG. 23, the position and the inclination of the probe 2 can be detected from lengths of respective wires 60*a*, 60*b*.

Figure 26:
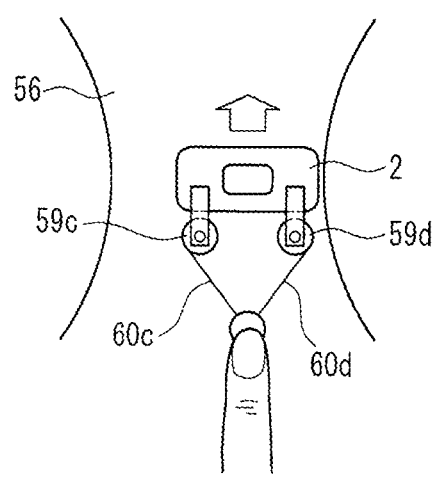
FIG. 26 is a top view showing another configuration of the ultrasound diagnostic apparatus according to Embodiment 10.

Further, as shown in FIG. 26, the ultrasonic probe may have a configuration in which two sets of the wire length detection mechanisms 59*c*, 59*d* are arranged side by side at different positions in the plane direction of the neck. Specifically, it is preferable to arrange these mechanisms in the direction vertical to the moving direction of the probe 2. In this configuration, the position of the probe 2 and the rotation angle of the probe 2 with respect to the plane direction of the neck can be detected from the lengths of respective wires 60*c*, 60*d*. Therefore, in the first scanning and the second scanning, it is possible to equalize the rotation angle of the probe 2 in the plane direction of the neck, and thus the accurate IMT can be measured.

Figure 27:
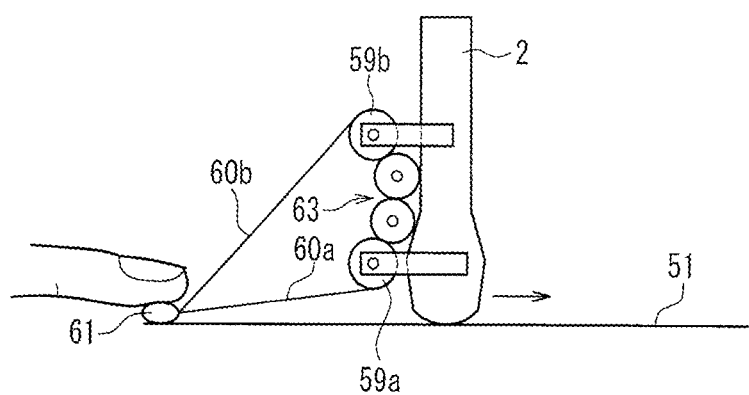
FIG. 27 is a side view showing another configuration of the ultrasound diagnostic apparatus according to Embodiment 10.

Further, as shown in FIG. 27, the ultrasonic probe may include a linkage mechanism 63 that links the rotations of the two bobbins to the two sets of the wire length detection mechanisms 59*a*, 59*b*. According to this configuration, when the probe 2 is moved such that the respective wires 60*a*, 60*b* are pulled, it is possible to move the probe 2 while keeping a predetermined angle of the probe 2.

Although in FIG. 27, the two sets of the wire length detection mechanisms 59*a*, 59*b* are arranged at different positions in the height direction of the probe 2, they may be arranged in the directions vertical to the height direction of the probe 2 and the moving direction of the probe 2. In this configuration, when the probe 2 is moved such that the respective wires 60*a*, 60*b* are pulled, it is possible to move the probe 2 while keeping the rotation angle of the probe 2 in a predetermined plane direction of the neck.

Embodiment 11

Figure 28:
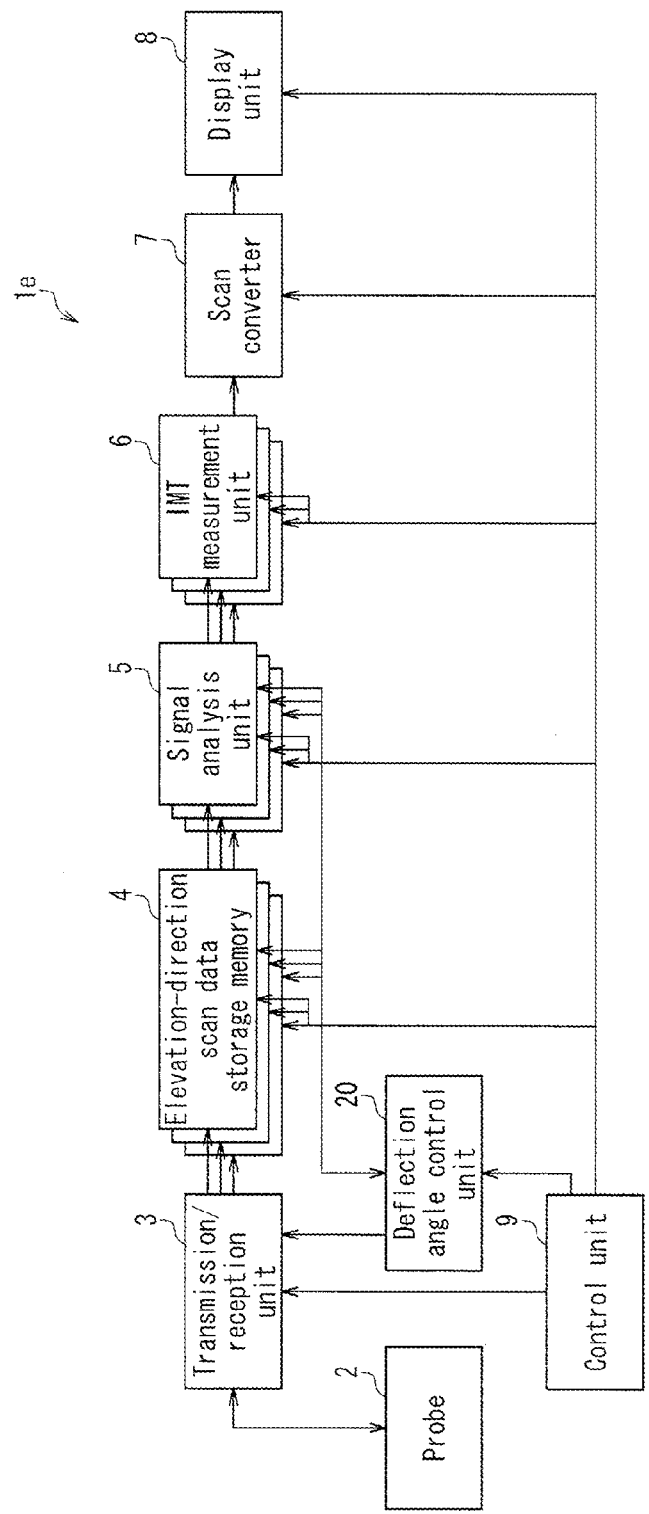
FIG. 28 is a block diagram showing a configuration of an ultrasound diagnostic apparatus according to Embodiment 11.
Figure 31:
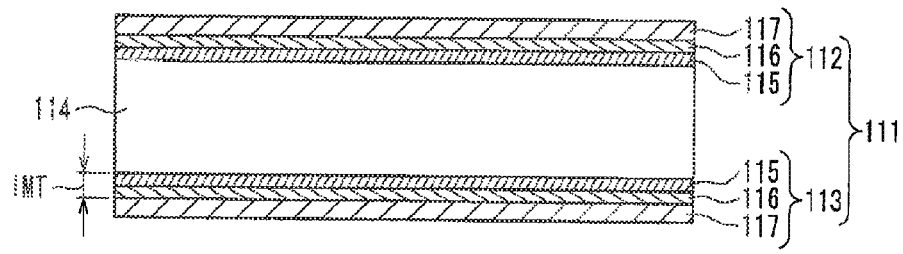
FIG. 31 is a cross-sectional view showing a configuration of a blood vessel.
Figure 32:
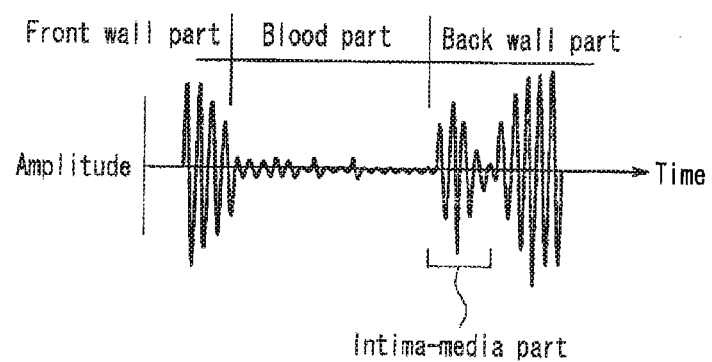
FIG. 32 is a waveform diagram showing a waveform of a scan line echo signal detected from echoes of ultrasonic beams irradiated to the blood vessel.
Figure 33:
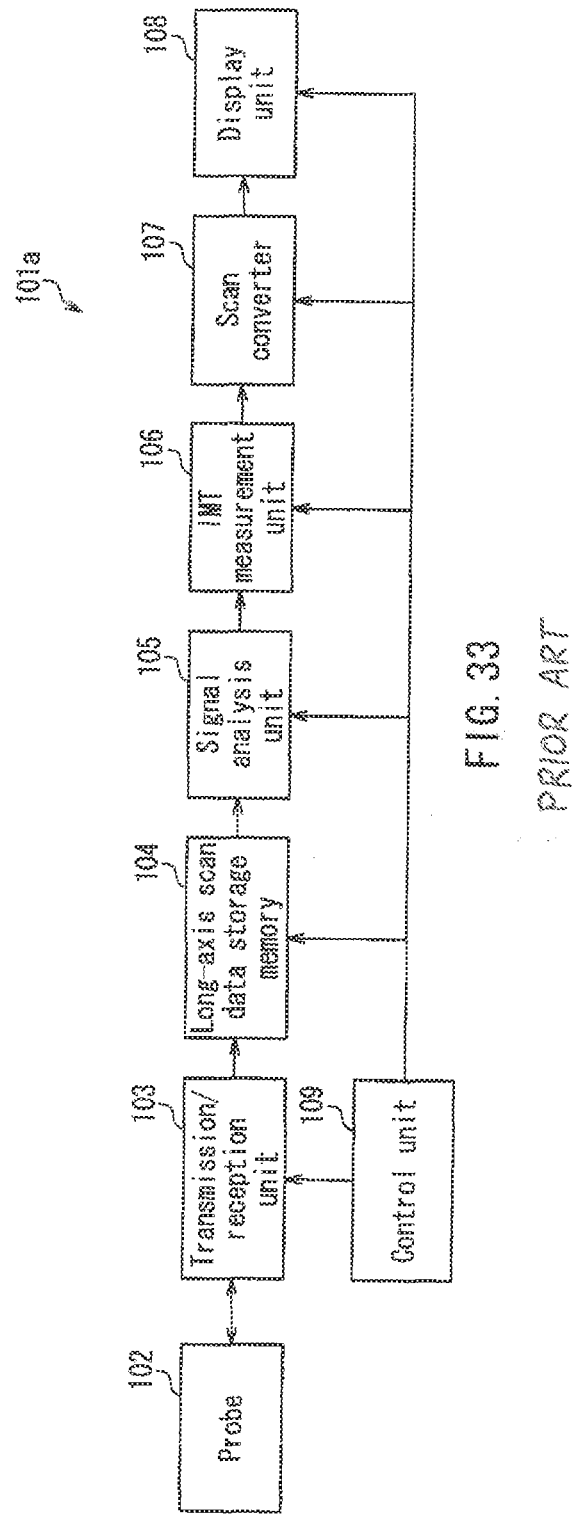
FIG. 33 is a block diagram showing a configuration of a first conventional ultrasound diagnostic apparatus.
Figure 34:
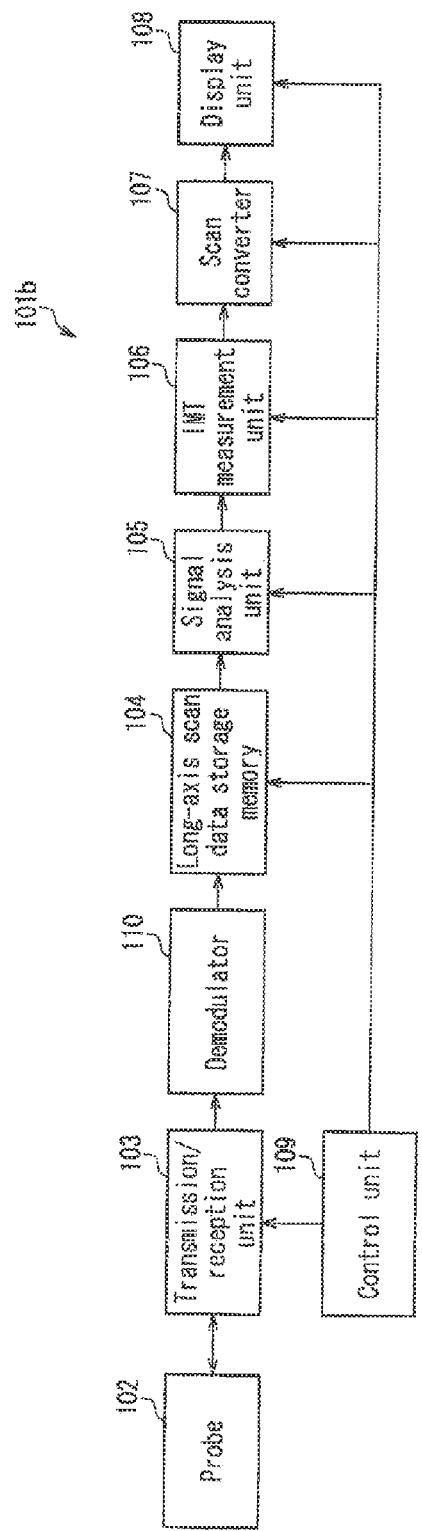
FIG. 34 is a block diagram showing a configuration of a second conventional ultrasound diagnostic apparatus.
Figure 35:
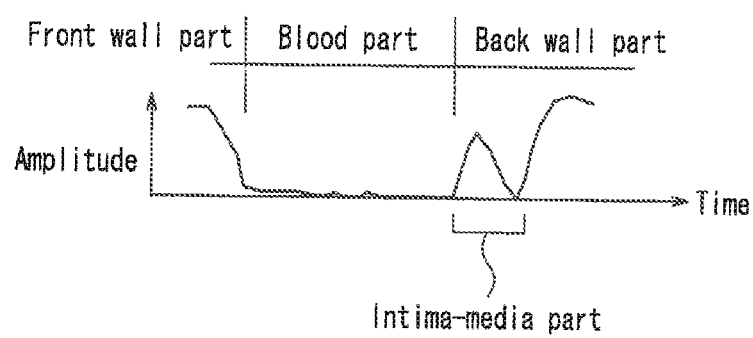
FIG. 35 is a waveform diagram showing a demodulation signal obtained at a demodulator in the second conventional ultrasound diagnostic apparatus.

FIG. 28 is a block diagram showing a configuration of an ultrasound diagnostic apparatus 1*e* according to Embodiment 11 of the present invention. The ultrasound diagnostic apparatus 1*e* according to the present embodiment is composed of three sets of the elevation-direction scan data storage memories 4, the signal analysis units 5 and the IMT measurement units 6 of the ultrasound diagnostic apparatus 1*a* according to Embodiment 1. The ultrasound diagnostic apparatus 1*e* also has a deflection angle control unit 20 that is connected to the transmission/reception unit 3, the elevation-direction scan data storage memories 4, the signal analysis units 5 and the control unit 9. The other constituent elements of the ultrasound diagnostic apparatus 1*e* are the same as those of the ultrasound diagnostic apparatus 1*a* according to Embodiment 1. The same constituent elements are denoted with the same reference numerals, and the explanation thereof will be omitted.

The ultrasound diagnostic apparatus 1*a* according to Embodiment 1 performs linear scanning. The ultrasound diagnostic apparatus according to the present embodiment performs scanning by changing the deflection angle of ultrasonic beams while changing the position of transducers (opening portion) emitting ultrasound in the array transducer. The deflection angle control unit 20 controls the deflection angle of ultrasonic beams.

Three sets of the elevation-direction scan data storage memories 4, the signal analysis units 5 and the IMT measurement units 6 are provided. By providing the three sets of these units, intima-media thicknesses at three locations can be detected by one scanning with respect to one scanning surface, whereby the IMT can be computed at the same time.

FIG. 29 is a view showing a positional relationship between an array transducer 64*a*, the blood vessel 21, and ultrasonic beams 65a-65c. FIGS. 29A, 29B and 29C show sequential states of scanning in the same scanning surface. FIG. 29A shows a state in which left transducers (opening portion) of the array transducer are driven, and the ultrasonic beam having a lower-right deflection angle is irradiated to the blood vessel. FIG. 29B shows a state in which center transducers of the array transducer are driven, and the ultrasonic beam having a downward deflection angle is irradiated to the blood vessel. FIG. 29C shows a state in which right transducers of the array transducer are driven, and the ultrasonic beam having a lower-left deflection angle is irradiated to the blood vessel.

By controlling the deflection angle as described above, the ultrasonic beams shown in the respective drawings pass through the center of the blood vessel. Therefore, echoes of the blood vessel wall (back wall) can be detected, and the intima-media thickness, i.e., IMT can be measured. In other words, it is possible to measure the IMT in different parts in the same cross section of the blood vessel.

Although, in the present embodiment, the scanning is realized by moving the opening and changing the deflection angle simultaneously using the array transducer arranged linearly, the present embodiment is not limited to this example. For example, when a concave array transducer 64b is used as shown in FIG. 30, ultrasonic beams 65d-65f can pass through the center of the blood vessel only by moving the opening, without the need to change the deflection angle. Thus, the above-described effect can be obtained.

Further, the ultrasound diagnostic apparatus of the present invention is useful for diagnosing cervical blood vessels, but is not limited to this. For example, it can be used for diagnosing blood vessels of a brachium, etc.

In each of the above-described embodiments, for example, an average value or a maximum value of intima-media thicknesses detected at a plurality of positions in the blood vessel is computed as the IMT. However, an intima-media thickness detected only at one position in the blood vessel also can be defined as the IMT.

INDUSTRIAL APPLICABILITY

The present invention has an effect of allowing the IMT measurement even when a blood vessel seen from a body surface is bent, and can be used as an ultrasound diagnostic apparatus for detecting an IMT in a cervical blood vessel, etc.

DESCRIPTION OF REFERENCE NUMERALS

1a-1e ultrasound diagnostic apparatus
2 probe
3 transmission/reception unit
4 elevation-direction scan data storage memory
5, 5a-5d signal analysis unit
6 IMT measurement unit
7 scan converter
8 display unit
9 control unit
10 blood part length measurement unit
11a-11d data detection unit
12 intima-media amplitude difference measurement unit
13 intima-media amplitude ratio measurement unit
14, 16 demodulator
15 differentiator
17 blood vessel inclination calculation unit
18 inclination control unit
19, 64a, 64b array transducer
20 deflection angle control unit
21 blood vessel
22 tunica adventitia
23 tunica media
24 tunica intima
25 blood
31 front wall part
32 blood part
33 back wall part
34 tunica intima part
35 tunica media part
36 tunica adventitia part
41 B-mode image
42 center region
43 combined image
51 body surface
52 attachment
53 rotation shaft
54 cervical blood vessel
55, 65a-65f ultrasonic beam
56 neck
57 photoelectronic sensor
58 tape
59, 59a-59d bobbin
60, 60a-60d wire
61 stopper
62 contact point sensor
63 linkage mechanism

The invention claimed is:

1. An ultrasound diagnostic apparatus, comprising:
a probe that transmits and receives ultrasound;
a signal analysis unit, wherein when the probe scans a cross section of a blood vessel perpendicular to a longitudinal axis of the blood vessel using the ultrasound, the blood vessel having a wall with concentrically arranged from outside the blood vessel a tunica adventitia, a tunica media, and a tunica intima, with blood flowing inside the tunica intima, the signal analysis unit receives a plurality of scan line echo signals from the probe, each having an amplitude corresponding to a reflected wave of the ultrasound from the blood and an amplitude corresponding to reflected waves of the received ultrasound from the wall at a front and a back of the blood vessel, detects, for each of the scan line echo signals, a maximum amplitude of the tunica intima and a minimum amplitude of the tunica media, measures, for each of the scan line echo signals, an amplitude difference between the maximum amplitude of the tunica intima and the minimum amplitude of the tunica media, and detects a center scan line echo signal from the plurality of scan line echo signals received from the probe, the center scan line echo signal is detected by detecting one of the plurality of scan line signals having a largest amplitude difference between the maximum amplitude of the tunica intima of the blood vessel and the minimum amplitude of the tunica media of the blood vessel, where the amplitude corresponding to the blood is smaller than the amplitude corresponding to the wall of the blood vessel; and
an intima-media thickness (IMT) measurement unit that computes an IMT from the center scan line echo signal.

2. The ultrasound diagnostic apparatus according to claim 1,
wherein, when the probe scans a plurality of cross sections of the blood vessel using the ultrasound, the signal analysis unit detects respective center scan line echo signals for each of the plurality of cross sections of the blood vessel, and the IMT measurement unit computes an IMT from the respective center scan line echo signals detected from the scan line echo signals.

3. An ultrasound diagnostic apparatus, comprising:
a probe that transmits and receives ultrasound:
a signal analysis unit, wherein when the probe scans a cross section of a blood vessel perpendicular to a longitudinal axis of the blood vessel using the ultrasound, the blood vessel having a wall with concentrically arranged from outside the blood vessel a tunica adventitia, a tunica media, and a tunica intima, with blood flowing inside the tunica intima, the signal analysis unit receives a plurality of scan line echo signals from the probe, each having an amplitude corresponding to a reflected wave of the ultrasound from the blood and an amplitude corresponding to reflected waves of the received ultrasound from the wall at a front and a back of the blood vessel, detects, for each of the scan line echo signals, a maximum amplitude of the tunica intima and a minimum amplitude of the tunica media, and measures, for each of the scan line echo signals, a ratio of the maximum amplitude of the tunica intima and the minimum amplitude of the tunica media, and detects a center scan line echo signal from the plurality of scan line echo signals received from the probe, the center scan line echo signal is detected by detecting one of the plurality of scan line echo signals having a largest ratio of the maximum amplitude of the tunica intima to the minimum amplitude of the tunica media of the blood vessel, where the amplitude corresponding to the part of the blood vessel containing the blood is smaller than the amplitude corresponding to the wall of the blood vessel; and
an intima-media thickness (IMT) measurement unit that computes an IMT from the center scan line echo signal.

4. The ultrasound diagnostic apparatus according to claim 3,
wherein, when the probe scans a plurality of cross sections of the blood vessel using the ultrasound, the signal analysis unit detects respective center scan line echo signals for each of the plurality of cross sections of the blood vessel, and the IMT measurement unit computes an IMT from the respective center scan line echo signals detected from the scan line echo signals.

* * * * *